United States Patent
Bulkes et al.

(10) Patent No.: US 7,917,213 B2
(45) Date of Patent: *Mar. 29, 2011

(54) MRI COMPATIBLE IMPLANTED ELECTRONIC MEDICAL LEAD

(75) Inventors: Cherik Bulkes, Sussex, WI (US); Stephen Denker, Mequon, WI (US)

(73) Assignee: Kenergy, Inc., Mequon, WI (US)

( * ) Notice: Subject to any disclaimer, the term of this patent is extended or adjusted under 35 U.S.C. 154(b) by 232 days.

This patent is subject to a terminal disclaimer.

(21) Appl. No.: 11/844,494

(22) Filed: Aug. 24, 2007

(65) Prior Publication Data

US 2008/0033497 A1 Feb. 7, 2008

Related U.S. Application Data

(63) Continuation-in-part of application No. 11/553,228, filed on Oct. 26, 2006.

(60) Provisional application No. 60/734,018, filed on Nov. 4, 2005, provisional application No. 60/949,763, filed on Jul. 13, 2007, provisional application No. 60/947,576, filed on Jul. 2, 2007, provisional application No. 60/912,451, filed on Apr. 18, 2007, provisional application No. 60/892,260, filed on Mar. 1, 2007.

(51) Int. Cl.
A61N 1/00 (2006.01)
(52) U.S. Cl. .......................................................... 607/9
(58) Field of Classification Search ....................... 607/9
See application file for complete search history.

(56) References Cited

U.S. PATENT DOCUMENTS 2,966,640 A * 12/1960 Eiland, Jr. ........................ 333/26
5,217,010 A * 6/1993 Tsitlik et al. ...................... 607/9
(Continued)

FOREIGN PATENT DOCUMENTS

WO 2006023700 A 3/2006
(Continued)

OTHER PUBLICATIONS

Environmental Chemistry.com list of Periodic Table of Elements as sorted by Electrical Conductivity, accessed Dec. 4, 2009. http://environmentalchemistry.com/yogi/periodic/electrical.html.*

(Continued)

*Primary Examiner* — George Manuel
*Assistant Examiner* — Robert N Wieland
(74) *Attorney, Agent, or Firm* — Quarles & Brady LLP; George E. Haas

(57) ABSTRACT

An implantable biocompatible lead that is also compatible with a magnetic resonance imaging scanner for the purpose of diagnostic quality imaging is described. The implantable electrical lead comprises a plurality of coiled insulated conducting wires wound in a first direction forming a first structure of an outer layer of conductors of a first total length with a first number of turns per unit length and a plurality of coiled insulated conducting wires wound in a second direction forming a second structure of an inner layer of conductors of a second total length with a second number of turns per unit length. The first and the second structures are separated by a distance with a layer of dielectric material. The distance and dielectric material are chosen based on the field strength of the MRI scanner. The lead may further comprise a conducting layer formed by coating a material consisting of medium conducting particles in physical contact with each other and a mechanically flexible, biocompatible layer forming an external layer of lead and in contact with body tissue or body fluids.

38 Claims, 8 Drawing Sheets

U.S. PATENT DOCUMENTS

| | | |
|---|---|---|
| 6,713,671 B1 | 3/2004 | Wang |
| 6,930,242 B1 * | 8/2005 | Helfer et al. .................. 174/36 |
| 7,363,090 B2 | 4/2008 | Halperin et al. |
| 2003/0036776 A1 | 2/2003 | Foster |
| 2003/0050557 A1 * | 3/2003 | Susil et al. .................. 600/424 |
| 2003/0144721 A1 * | 7/2003 | Villaseca et al. ............. 607/122 |
| 2004/0014355 A1 * | 1/2004 | Osypka et al. ................ 439/502 |
| 2004/0199069 A1 * | 10/2004 | Connelly et al. ............. 600/412 |
| 2004/0230271 A1 * | 11/2004 | Wang et al. .................. 607/116 |
| 2008/0195187 A1 * | 8/2008 | Li et al. ....................... 607/116 |
| 2009/0171421 A1 * | 7/2009 | Atalar et al. .................. 607/63 |

FOREIGN PATENT DOCUMENTS

| | | |
|---|---|---|
| WO | 2006093685 A | 9/2006 |
| WO | 2006105066 A | 10/2006 |

OTHER PUBLICATIONS

Properties of Nitinol webpage, accessed Dec. 4, 2009. http://www.peiertech.com/Literature/Properties%20of%20Nitinol.pdf.*

* cited by examiner

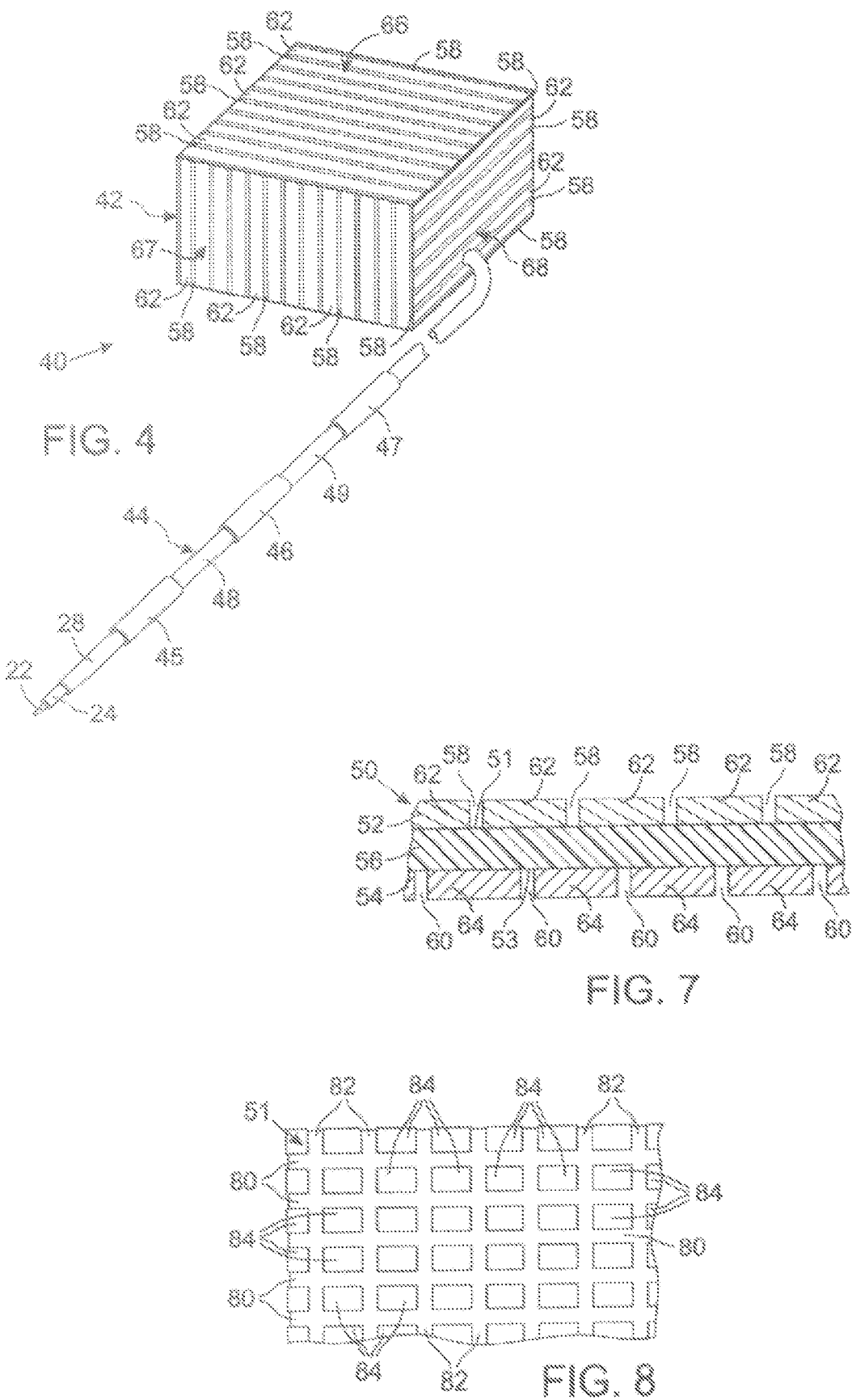

MRI COMPATIBLE IMPLANTED ELECTRONIC MEDICAL LEAD

CROSS-REFERENCE TO RELATED APPLICATIONS

This application is a continuation-in-part of U.S. patent application Ser. No. 11/553,228 filed on Oct. 26, 2006; and claims benefit of U.S. Provisional Patent Applications No. 60/734,018 filed Nov. 4, 2005, No. 60/892,260 filed Mar. 1, 2007, No. 60/912,451 filed Apr. 18, 2007, No. 60/947,576 filed Jul. 2, 2007, and No. 60/949,763 filed Jul. 13, 2007.

STATEMENT REGARDING FEDERALLY SPONSORED RESEARCH OR DEVELOPMENT

Not Applicable

BACKGROUND OF THE INVENTION

1. Field of the Invention

The present invention relates implantable electronic medical devices, such as cardiac pacemakers and defibrillators for example, for stimulating tissue of animal for the therapeutic purposes, and such implantable medical devices that are compatible with magnetic resonance imaging (MRI).

2. Description of the Related Art

Numerous medical conditions, such as cardiac and neurological dysfunctions, are treated by an implanted electronic device which provides electrical stimulation to the affected tissue of the animal. These devices have a plurality of metal components, including the generator case and wire leads extending from the case to electrodes in contact with the tissue to be stimulated or monitored.

Magnetic resonance imaging (MRI) is commonly employed to view internal organs of medical patients. To create an image, the patient is placed into very strong static and varying magnetic and radio frequency (RF) fields and thus MRI generally is prohibited for patients with implanted ferromagnetic and or electrically conductive objects. Although it is feasible to minimize and even eliminate the use of ferromagnetic materials in implanted apparatus, electronic devices, such as cardiac pacemakers and defibrillators, require electrically conductive components that are affected by the fields produced by an MRI scanner.

It has been a long-standing goal to make implanted devices MRI compatible so that this imaging modality can be used with patients having those devices. There are several reasons for achieving this goal. First, incompatible implant components induce susceptibility difference, which destroys DC magnetic field homogeneity, thereby affecting the imaging performance of the magnetic resonance scanner. Second, conductive materials present an opportunity for eddy currents to form, which currents generate heat that adversely affects patient safety and degrade the scanner performance by field distortion. Third, the MRI fields may ruin the implanted device. Fourth, the incompatible implant material can potentially cause serious internal injuries to the patient.

The issue of MRI interaction with electronics of an implanted device has to be considered in an integrated fashion to provide compatibility. Table 1 shows combinations of interactions that are briefly discussed hereinafter.

TABLE 1

Interactions of Factors Influencing MRI Compatibility of an Implanted Device or Component

|  | Patient Safety | Effect on the Implanted Device | Effect on the MR Image |
| --- | --- | --- | --- |
| DC Magnetic Fields | I | II | III |
| Gradient Magnetic Fields | IV | V | VI |
| RF Fields | VII | VIII | IX |

I. Any ferromagnetic material inside the implanted device exposed to the MRI fields experiences a force and a torque, the amount of which depends on the shape, dimensions, and amount of ferromagnetic material. The forces are greatest in areas where there is a gradient in the magnetic field, e.g. upon entering a MRI system. Obviously the surrounding tissue adjacent the implantable device will be damaged in this case and the health of the patient will be compromised. In addition, metallic components can become hot and burn the patient.

II. Due to MRI field induced torque and movement of the implant, its components may become disconnected making the device inoperable. Ferrites and other ferromagnetic material in transformer cores, inductors and other electronic components become saturated, thereby jeopardizing the function of the medical device. Heating causes electronic components to operate out of specification.

III. The homogeneity of the magnetic resonance imager's DC magnetic field will be distorted, destroying spectral resolution and geometric uniformity of the image. The inhomogeneous field also results in rapid de-phasing of the signal inside the excited volume of the patient. The resultant image shows a distorted view of the patient's anatomy.

Even if the implanted device does not contain any ferromagnetic materials, the magnetic susceptibility of the device may be different than that of the surrounding tissue, giving rise to local distortion and signal dropouts in the image, close to the device. This is especially true for pulse sequences that are sensitive to phase, like echo planar imaging IV. Switching field gradients create large eddy currents, at frequencies up to a few kilohertz, in the metallic housing of an implantable device and any metallic part that forms a loop, such as cables forming a loop. These eddy currents make the device move with the same frequency as the leading and trailing edges of gradient pulses. This movement can be unsafe for the surrounding tissue. The associated eddy current pattern creates local pulsating E-fields, in addition to the E-field generated by the MRI scanner's gradient coil, which can stimulate the patient's nerves. Resultant muscle twitching can be so intense as to be painful.

V. The eddy currents may be strong enough to damage electronic circuits and destroy the implanted device. The pulsating forces on the device may disconnect components.

VI. The eddy currents affect the rise time of the MRI gradient pulses, and therefore affect the minimum obtainable echo time, necessary for many pulse sequences. The eddy currents also locally distort the linearity of the gradient fields and de-phase the spin system, resulting in image distortion and signal dropouts. Phase and frequency encoding of the signal strongly depends on the linearity of the gradients.

VII. The RF field interacts with any metallic part in the device, be it either in the form of a loop, which results in B-field coupling, or a straight conductor, which results in E-field coupling. The B-field component of the RF field can induce currents and voltages in conducting loops. The amplitude depends on the impedance of the loop at the RF frequency, and the size of the loop. An example may be two coaxial cables that form a loop together. Such a loop may have high impedance at DC due to the insulating outer shell of the coax, but the distance between the cables at the crossover point may be equivalent to just the right amount of capacitance to make the loop resonant at the RF frequency.

The E-field component of the RF field will induce voltages and currents in straight conductors, like a single cable for example. The amplitude of the induced voltages and currents depends on the phase length of the conductor, or path, at the associated radio frequency.

The induced voltages and currents create locally very strong E-fields that can burn the patient.

Non-metallic implantable devices do not have these issues, but can still distort the uniformity of the RF field if the permittivity of the device is different than that of the surrounding tissue. This distortion is especially strong at radio frequencies above 100 MHz.

VIII. Localized high voltages and currents in the medical device may cause components to fail either due to high voltage arcing, or due to dissipated power and heat. This includes connections that become unsoldered due to the heat. The device may generate pulsed voltages at unwanted times and locations in the leads of a cardiac pacemaker.

IX. Local distortion of the uniformity of the B-field component of the RF field will give rise to flip angle variation and creates contrast and signal-to-noise ratio (SNR) inhomogeneity. The specific absorption rate, which is defined as the RF power absorbed per unit of mass of an object, can exceed legal limits. If the specific absorption rate exceeds legal limits, images cannot be made using magnetic resonance scanners.

From a fundamental physical perspective, it is useful to examine the conductivity of wires at high frequencies of MRI. As frequencies increase, conduction begins to move from an equal distribution through the conductor cross section toward existence almost exclusively near the surface. Depending on the conductor bulk resistivity, at sufficiently high frequency all the RF current is flowing within a very small thickness at the surface. Lower bulk resistivities result in shallower skin depths.

For a solid wire, the current concentrates on the outer surface. For this reason, when skin depth is shallow, the solid conductor can be replaced with a hollow tube with no perceivable loss of performance. Choice of a plating material can degrade performance (increase attenuation) if its bulk resistivity is greater than that of the body of the wire. If such a conductor is placed inside the E field of an MRI RF Transmit coil, there will be RF energy deposition in the tissue surrounding the wire resulting in elevated temperatures that may result in physical injury to the patient.

Therefore it is desirable to provide an integrated, comprehensive solution to MRI compatibility of an implanted medical device that contains electronics circuitry. Furthermore, it is desirable to make leads that connect implanted medical devices to the electrodes for stimulation therapy and/or electrical sensing MRI compatible.

SUMMARY OF THE INVENTION

This invention is directed toward an implantable biocompatible lead that is also compatible with a magnetic resonance imaging scanner for the purpose of diagnostic quality imaging. The implantable electrical lead comprises a plurality of coiled insulated conducting wires wound in a first direction forming a first structure of an outer layer of conductors of a first total length with a first number of turns per unit length and a plurality of coiled insulated conducting wires wound in a second direction forming a second structure of an inner layer of conductors of a second total length with a second number of turns per unit length. The first and the second structures are separated by a distance with a layer of dielectric material. The distance and dielectric material are chosen based on the field strength of the MRI scanner. The lead may further comprise a conducting layer formed by coating a material consisting of medium conducting particles in physical contact with each other and a mechanically flexible, biocompatible layer forming an external layer of lead and in contact with body tissue or body fluids. In one embodiment the conductive layer can also be the mechanically flexible, biocompatible layer. In one embodiment the conductive layer is formed on the first structure of outer layer of conductors. In another embodiment, the conductive layer is formed on the second structure of inner layer of conductors. In one embodiment of this invention, the winding direction of outer insulated conductors is the same as the winding direction of the inner insulated conductors. In another embodiment of this invention, the winding direction of outer insulated conductors is different than the winding direction of the inner insulated conductors.

In one embodiment, the lead is part of an electrical stimulation system. In another embodiment, the lead is part of a cardiac pacing system. In yet another embodiment, the lead is part of a cardiac defibrillation system.

The invention also contemplates an implantable defibrillation lead compatible in a magnetic resonance imaging scanner for the purpose of diagnostic quality imaging. The implantable defibrillation lead comprises a plurality of coiled insulated conducting wires wound in a first direction forming a structure of an outer layer of conductors wherein at least two of insulated conductors come out of the lead body without insulation and are wound on the lead body without touching each winding of the coil as electrodes, a plurality of coiled insulated conducting wires wound in a second direction forming a structure of an inner layer of conductors wherein the structure forming inner layer of conductors and the structure forming the outer layer of conductors have a common central axis and a conducting layer formed by coating a material consisting of medium conducting particles in physical contact with each other.

BRIEF DESCRIPTION OF DRAWINGS

FIG. 4 illustrates an electrical lead extending from a medical device housing to stimulation electrodes;

FIG. 7 is a cross section through a wall of a medical device housing showing slots in conductive layers that prevent formation of gradient eddy currents;

FIG. 8 is a plane view of an alternative configuration of slots in the surface of the medical device housing;

DETAILED DESCRIPTION OF THE INVENTION

Figure 1:
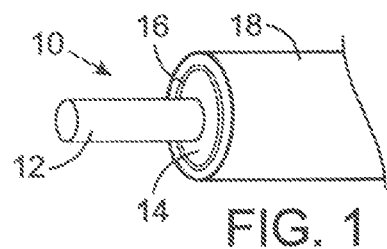
FIG. 1 is an isometric view of a conventional coaxial cable that is used as an medical device lead.

The present technique for MR compatibility of an implanted electronic medical device considers several effects of direct current (DC) magnetic fields, gradient magnetic fields, and RF fields on patient safety, the implanted device and the MRI scanner. As a consequence, the medical device incorporates one or more mechanisms that offer high impedance to currents induced by the MRI electromagnetic fields or prevent such currents from forming in the first place. These mechanisms comprise non-ferromagnetic components which have a magnetic susceptibility close to that of the surrounding tissue; electrical leads with traps for MRI induced currents; and a housing formed by a plurality of electrically conductive segments that combine to provide RF shielding of internal circuit while not providing large enough areas for formation of eddy currents. As used herein, a "trap" is a circuit element that either blocks current induced by the MRI fields or significantly attenuates that currents to a level at which the current does not cause an adverse effect to the animal being scanned.

The cable traps are placed along the cable to provide high impedance to radio frequency currents induced in the cable while presenting low impedance to direct current of stimulation pulses produced by the medical device. Such traps provide sufficiently high impedance, reactance and/or resistance, to prevent induced current from forming during MRI radio frequency pulses in the 1-500 MHz range.

A terminating element at the lead to stimulator circuit interface, which provides high impedance at the gradient rise time frequency (e.g. 1-10 KHz), but low impedance at the frequency of the generated pulses or sensed cardiac signal, eliminates currents induced on the lead by the E-field produced by the gradient coils in the MRI system. One embodiment employs parallel resonant networks, such as bazooka baluns, to prevent standing waves on the shield of the cable. With a balun configuration, one may include small, rigid stress relief points along the lead at pre-determined distances since a device lead, for example, a pacemaker lead, may make several turns and loops. The reason for putting rigid pieces in is to keep the resonance frequency of the balun constant. In a flexible structure the frequency of the balun would move around too much, especially if it is a self resonant structure. As an alternative to a balun, at least one PIN diode is placed along the cable and selectively forward and reverse biased by a DC control voltage to act as a switch. The PIN diode is rendered conductive during stimulation pulses produced by the medical device and is non-conductive at other times. A micro electro-mechanical system (MEMS) is another type of switch that can be used. The DC leads also need to present high impedance at the RF frequency, which can be accomplished via chokes, or resistors, if the diode or MEMS switch uses low current.

In an embodiment, lead design is based on transmission line type architecture with a characteristic phase rotation along the length of the transmission line. The parameters to characterize the lead's electrical characteristic include varying pitch, turn to turn distance, coaxial radial spacing, permittivity of dielectric and number of layers. Having more turns per centimeter will increase inductance and capacitance. Increasing turn to turn spacing will decrease parasitic capacitance. By adding a second coaxially wound layer creates a classic coax transmission line topology. The resultant circuit structure resembles a chained LC network, with the primary inductance being in the layers and the capacitance between the layers. In this arrangement, turn to turn capacitance will also be present. The effect of "global" capacitance rather than turn to turn capacitance is enhanced by winding the second layer opposite from the inner layer, i.e., if the inner layer is wound clockwise (CW), then the outer layer is wound counter clockwise (CCW).

The electrical length of the lead is a function of a wavelength of interest which is determined by the velocity of the electromagnetic wave in the animal tissue divided by the frequency of the electromagnetic wave. The velocity is the inverse of the square root of the product of permittivity and permeability of the tissue. Preferably the electrical length of the lead is an odd multiple of a quarter wavelength of interest for a 1.5 Tesla (T) MRI scanner operating at 64 MHz or a 3.0 T MRI scanner operating at 127.7 MHz. The same applies to any other frequency, although 1.5 T and 3.0 T are the primary field strengths for clinical use. It is further designed to be electrically open or high impedance (typically the driven end of the lead) at one end and almost shorted at the other end (typically the stimulating end of the lead). In this context, the term "almost shorted" refers to low impedance of 3-5 ohms at 64 MHz.

In some embodiments that are contemplated in the current invention, special considerations need to be taken to ensure MRI compatibility. These considerations may include avoiding loops in the lead at all times unless the distance at the crossover point between the two ends of the lead forming a loop, is larger than approximately ten lead diameters.

The metallic housing, for the medical device's electronic circuitry, is separated into a plurality of overlapping electrically conductive segments that are insulated from one another. The result is a housing that offers high impedance for signals up to 200 KHz and acts as a continuous shield for RF signals. Since traps are narrow band devices, they need to be tuned to the Larmor frequency of the MRI scanner. The RF shielding is due to the capacitance coupling between the electrically conductive segments.

With initial reference to FIG. 1, a conventional coaxial cable 10 includes a center conductor 12 surrounded by a cylindrical enclosure 14 of a suitable dielectric material. A cylindrical electrically conductive shield 16 that surrounds the cylindrical enclosure 14 and is encased in an insulating outer cover 18.

Figure 2:
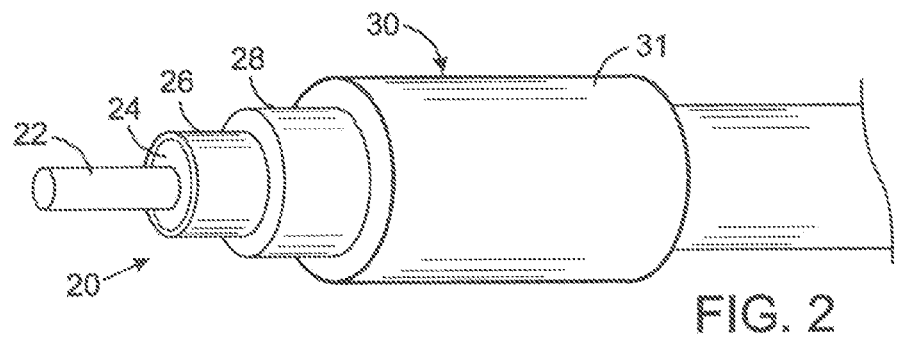
FIG. 2 is an isometric view of a tri-axial cable that has been modified with novel traps to prevent interaction with external RF fields of an MRI scanner.

FIG. 2 illustrates a modification of a standard tri-axial cable according to the present invention to form a coaxial cable with traps for signals induced in the cable by an MRI scanner. The traps impose high impedance to the common mode current induced in the cable by the E-field of an MRI radio frequency body coil. The modified tri-axial cable 20 comprises a central, first conductor 22 surrounded by a first tubular insulator 24 of a conventional dielectric material. A tubular second conductor, or inner shield, 26 extends around the first tubular insulator 24 to form an inner shield and is in turn surrounded by a second tubular insulator 28 of the dielectric material.

A standard tri-axial cable further comprises a tubular outer shield 32 of an electrically conductive material extending around the second tubular insulator 28 for the entire length of the cable. The resultant triaxial structure is encased in an insulating outer cover.

Figure 3:
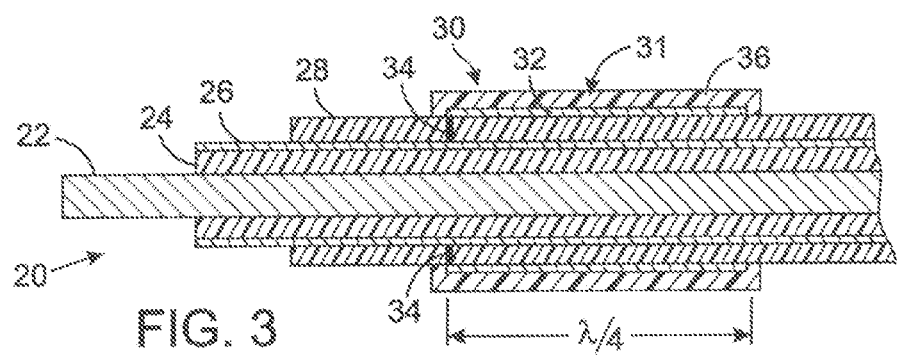
FIG. 3 is a longitudinal cross section of a portion of the tri-axial cable.

The tri-axial cable 20 in FIGS. 2 and 3 is a standard cable tri-axial that has been modified by cutting the tubular outer shield 32 and outer insulating cover 36 into a series of short sections. Those sections form traps 30 for common mode current induced in the cable by an MRI scanner. In the embodiment of FIG. 3, each trap 30 comprises a bazooka balun 31 connected to the remaining cable layers, thereby forming a parallel resonant network connected to a two conductor coaxial cable. The electrically conductive tubular outer shield 32 is cut to a longitudinal length that is identical to one-quarter of the wavelength ($\lambda$/4) of an RF frequency for which immunity is desired. This is an RF frequency emitted by the magnetic resonance scanner. As will be described, the cut sections of the outer shield 32 form networks each having an inductor connected in parallel with a capacitor, wherein the LC networks are tuned to different MRI frequencies. One end of each outer shield section is shorted by shunts 34 to the tubular second conductor 26, and the opposite section end is disconnected from the first and second conductors 22 and 26. This forms a standard bazooka balun 31 that is attached to the remaining cable elements 22-28 which function as a coaxial cable. The second tubular insulator 28 now also serves as the outer covering of that coaxial cable. The insulating outer cover 36 encloses the tubular outer shield 32 and preferably has its ends sealed to the second tubular insulator 28 to prevent short circuits.

A bazooka balun may be used for devices for implantation in vasculature of an animal, since the compact diameter of a tri-axial cable occupies relatively small volume of a blood vessel. However, other types of baluns could be used as the traps depending on the intended location of the cable. Examples of other baluns include a cable trap balun, where the cable is looped as a solenoid, and a parallel capacitance connects the grounds before and after the solenoid, thus forming a parallel resonator with high impedance at the frequency of interest. The bridge or lattice balun consisting of a network of two capacitors and two inductors also may be used.

FIG. 4 shows a modified tri-axial cable 20 used as a lead for stimulation electrodes of an implantable medical device 40, such as a cardiac pacemaker or defibrillator. The medical device 40 has electronic circuitry contained in a housing 42 from which a modified tri-axial cable 44 extends. That cable 44 has a plurality of bazooka baluns 45, 46 and 47 with coaxial cable sections 48 and 49 located there between. At the remote end of the cable 44 from the housing 42, the central, first conductor 22 and the second conductor 26 are exposed to form bipolar electrodes for applying DC stimulation pulses to the tissue of the animal in which the device is implanted. Alternatively the central, first conductor 22 and the second conductor 26 can be connected to other forms of electrodes that are adapted for placement in or against particular anatomical features of the animal.

Alternatively, each trap 30 can be formed by a choke placed along the cable at intervals equal to at least a quarter wavelength ($\lambda$/4) determined by the Larmor frequency (e.g. 64 MHz at 1.5 T) of the MRI scanner. The chokes impose high impedance at radio frequencies, but low impedance to DC.

Figure 5:
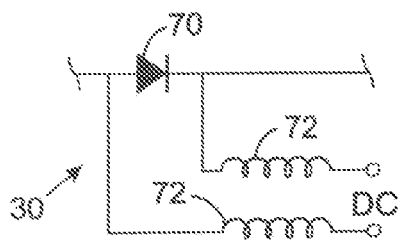
FIG. 5 is a circuit diagram of a second type of trap for the electrical lead.

If a high degree of isolation of the cable to MRI induced currents is desired, PIN diodes 70 can be placed at quarter wavelength intervals along the cable. As shown in FIG. 5, each PIN diode 70 is forward biased by a DC control voltage during a stimulation pulse and reverse biased by that DC control voltage when RF immunity is desired, such as during MRI scan pulses. This embodiment requires additional cable conductors that are decoupled by chokes 72 and consume power from the medical device to bias the PIN diodes during long time periods.

Figure 6:
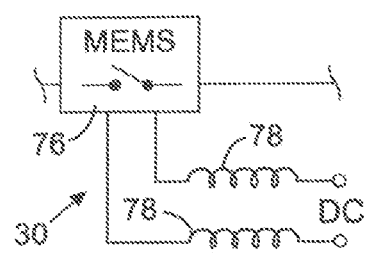
FIG. 6 is a circuit diagram of a third type of trap for the electrical lead.

A further alternative, that provides a high degree of isolation, places a standard micro electro-mechanical system (MEMS) switch 76 at each trap location along the cable as depicted in FIG. 6. The MEMS is a miniaturized RF switch that does not require a large current to close, unlike the large forward bias current required for a PIN diode. However, additional cable conductors and decoupling chokes 78 still are required. Due to the low power consumption of the MEMS, resistive wire may be used to supply the MEMS with DC. The above two solutions require extra wires that now will also need to be decoupled.

In an embodiment, leads are designed to be a quarter wavelength transmission line at 64 MHz for a 1.5 T MRI scanner or at 127.7 MHz for a 3 T MRI scanner. In addition, the quarter wavelength transmission line is shorted at the end, and, therefore, forms high impedance at the other end. Generally, the pitch, layer diameters and wire size are determined by electrical and mechanical design consideration to make the lead mechanically flexible and durable.

Figure 9A:
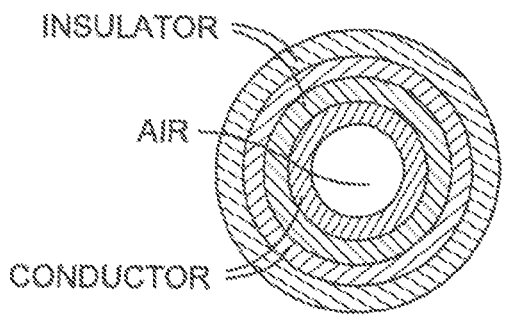
FIG. 9A is a cross sectional view of the electrical lead.
Figure 9B:
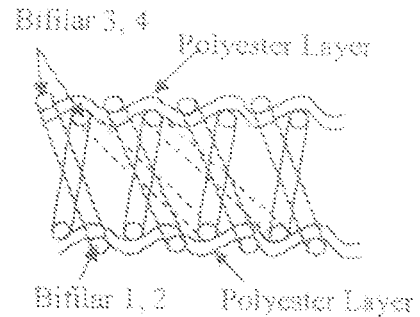
FIG. 9B is a longitudinal view of the electrical lead.

A first example of a transmission line lead is a multi filar lead using various pitches and diameters. Note that a dual bifilar is discussed here, but other combinations are possible as well to increase the total number of conductors. The examples for the purpose of clarity will show a dual bifilar configuration. As shown in the schematic of FIG. 9A, this lead configuration has an air core to allow for a guide wire in one embodiment. A first conductor layer containing bifilar conductors 1 and 2 is separated from a second conductor layer containing bifilar conductors 3 and 4 by a suitable dielectric material (e.g., polyester). The second conductor layer is covered by an insulator/biocompatible material (e.g., urethane) to prevent external surface from coming in contact with body fluids (e.g., blood). In one embodiment, the insulating material is shrink-wrapped around the layers of bifilar conductors as shown in FIG. 9B. This design not only improves the structural integrity of the lead but also provides ample space for an air core for allowing insertion of a guide wire. However, care should be taken in this design to prevent any body fluid from entering at the ends of the lead. It should be noted that electrical properties of the lead are dependent on the inner insulation thickness as well as the permittivity of the insulating material. Further it should be noted that the inductance of the lead increases with increased diameter of the helix of bifilar (or multifilar) conductors. In practice, however, this diameter cannot be arbitrarily varied since it is fixed due to the restriction imposed on the dimensions of an intravascular lead structure. In any case, inner layer of conductors may be used for delivering stimulation in one embodiment while the outer layer of conductors may be used for transmitting back physiological parameters and other relevant data.

Figure 9C:
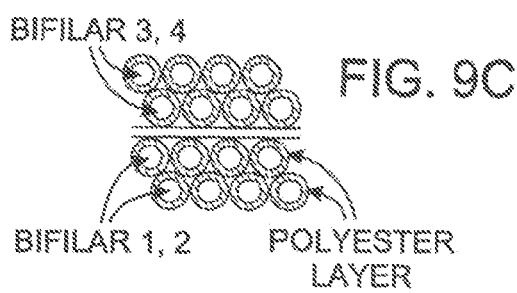
FIG. 9C is a longitudinal view of an alternative arrangement.

While this design differs from the traditional design of bifilar conductors shown in FIG. 9C in which each conductor is individually shrink wrapped with an insulating material. This design requires more insulating material and is mechanically less robust. However, this design completely insulates the conducting wire from coming in contact with body fluids.

Figure 10:
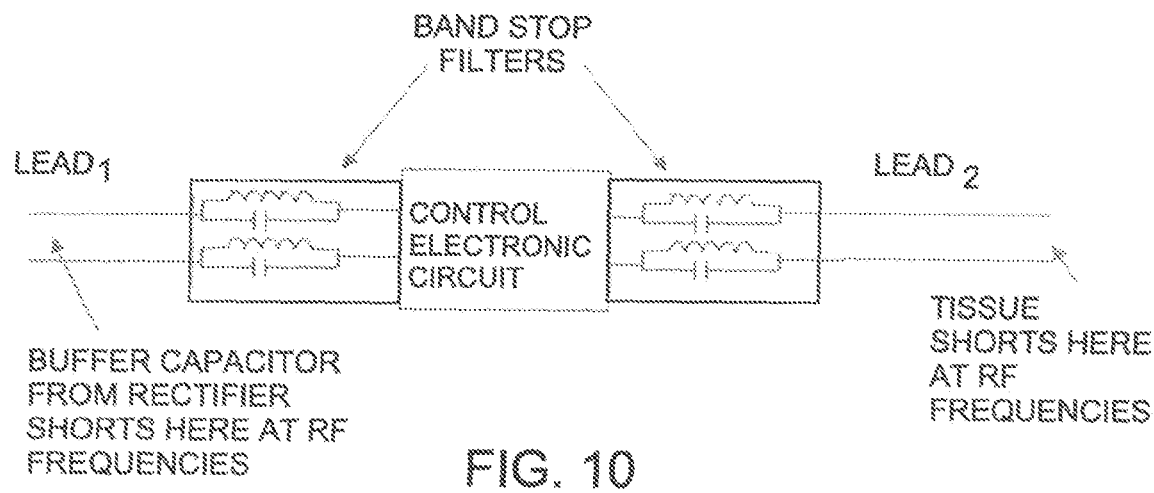
FIG. 10 is a schematic of the electrical lead and electronic circuit interface and lead and tissue interface.

In any case, the lead design should be such that at the RF frequency of interest it presents high impedance toward the electronic capsule and low impedance at the stimulating end of the lead. As shown in FIG. 10, the control electronic circuit module has bandstop (i.e., at the MR frequency) filters at the end connecting the control electronics circuitry. The length of lead1 and lead2 on opposite sides of the control electronic circuitry may be unequal in physical length but they need to be an odd multiple of quarter wavelength corresponding to 90, 270, 450 . . . degrees.

A second example of a transmission line lead may have a bifilar configuration. A bifilar clockwise, with coaxial bifilar counterclockwise lead can have controlled spacing between the coaxial layers wherein turns create inductance and the clock wise/counter clockwise layers will create a coaxial capacitor. The actual model is far more complex due to various coupling paths (inductive and capacitive). However, this design may provide a better level of control over the parameters of interest The transmission line's electrical length is tuned by building the lead from sections that are strung together to create L's, C's and R's using a two-step process. First, a conventional model is derived to determine locations and values of the resonant circuits along the lead. Second, components are created from lead topologies to create equivalent values. In an alternative method, one can create a plurality of physical models based on various parameters mentioned and measure the output to derive appropriate resonant circuit using well known statistical techniques. See a standard six sigma reference book for reference (*The Six Sigma Handbook* by Thomas Pyzdek, McGraw-Hill, 2000).

In a preferred embodiment of the present invention, RF energy deposition to the patient around a conductor is minimized by surrounding it with a physical layer that is neither a high conductor nor a high insulator. One aspect of the invention is to make a lead assembly in which one or more lead conductors individually or as a group have an RF energy dissipation and/or quenching layer made of a semi-conducting material. While we describe the RF energy dissipation and/or quenching layer around a conductor, it should be understood that RF energy dissipation and/or quenching layer can be advantageously added to any metallic implant coming in contact with a patient's tissue. For example, in orthopedic implants, if highly conductive materials are needed, they can be coated with a layer of RF energy dissipation and/or quenching material. As another example, if conductive stents are needed they can be rendered MRI compatible using a layer of semi-conducting material during the stent forming process. Such a semi-conducting material may be formed using various methods described below.

Figure 11A:
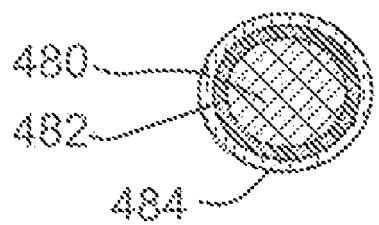
FIG. 11A is a schematic of the cross sectional view of a electrical lead assembly.
Figure 11B:
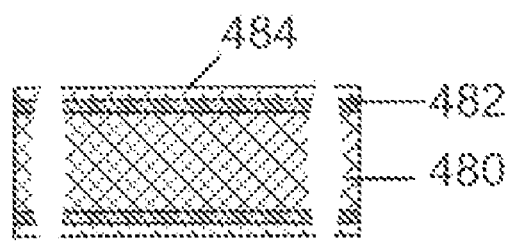
FIG. 11B is a longitudinal view of the electrical lead assembly.

Referring to FIG. 11A, the cross sectional view of the basic lead structure in the inventive subject matter has a single conductor 480 with an energy dissipation and/or quenching semiconducting layer 482. Additional biocompatible layer 484 may be formed as in a traditional implantable electrical lead. FIG. 11B is a longitudinal view of the lead assembly wherein the RF energy dissipation and/or quenching layer is formed around the central conductor.

Figure 12A:
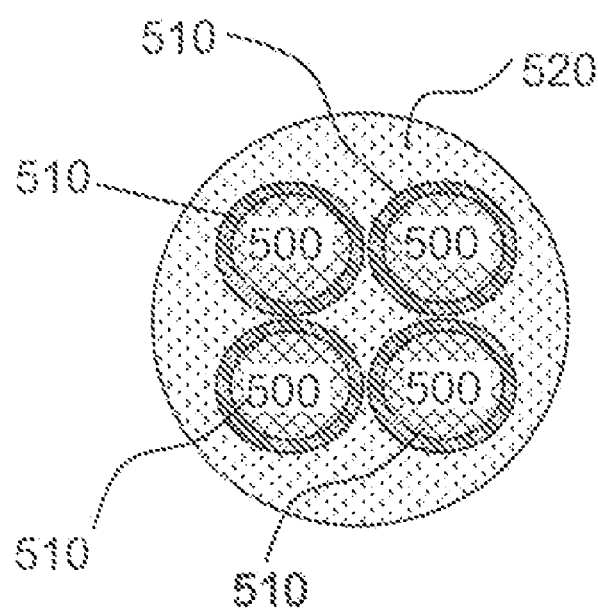
FIG. 12A is a schematic of the cross sectional view of the lead assembly with each conducting wire individually covered by a medium conductivity material.
Figure 12B:
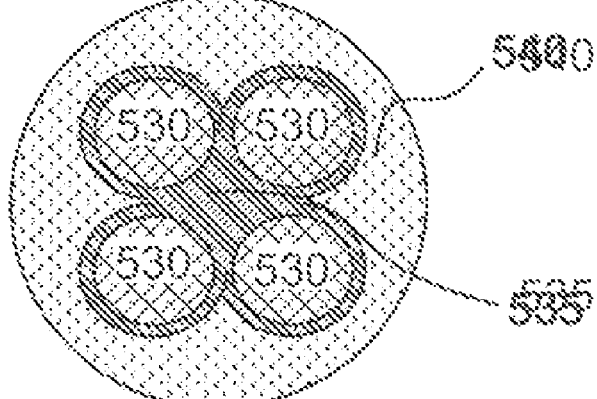
FIG. 12B is a cross sectional view of the lead assembly wherein the entire assembly is coated by medium conductivity material.

In FIG. 12A an arrangement of multiple conducting wires (e.g., quad-filar) is described. In one embodiment, each conductor 500 may have a layer of RF energy dissipation and/or quenching material 510 and there can be a common biocompatible layer 520. In an alternative embodiment shown in FIG. 12B, multiple conductors 530 may have a common RF energy dissipation and/or quenching material layer 535. Additionally, an additional biocompatible layer 540 is formed as in a traditional implantable electrical lead. The thickness of the layer may be adjusted based on the frequency of MRI application and may be based at least in part on the skin depth of the semi-conducting material.

RF Energy Dissipation and/or Quenching Materials:

The choice of the RF energy dissipation material mainly depends on the application at hand. It is also desirable that the RF energy dissipation material does not break off during chronic use and cause bio-hazard or other complications. In the following, a number of suitable candidate materials are described.

Carbon particles densely embedded in a polymer such as polyurethane may be used as an RF energy dissipation or quenching material. For this material to work, the carbon particles embedded in the polymer need to be touching each other to create a conductive layer. The density of the carbon particles may have to be adjusted to achieve the desired objective. Alternatively, graphite embedded in a rubber compound may be sprayed on to the conductors for a desired thickness. Alloys that have conductivity properties similar to that of graphite can be used as well. Semi-conducting materials such as germanium can be used as a coated layer around the conductor. In general, the desired electrical conductivity for the RF energy dissipation material is in the range of $10^{-2}$ to $10^4$ Siemens per meter (S/m).

Another class of suitable materials is conducting polymers that have been a focus of attention among researchers for more than two decades, since the discovery of doped polyacetylene in the 1970's. Their relatively large conductivity, light weight and flexibility are just some of the factors that make conducting polymers much more desirable than metals in certain applications. Of the various conducting polymers studied, polyaniline (PANi) has been investigated the most due to its ease of synthesis, relatively high conductivity and good stability. Depending on the oxidation level, PANi can be synthesized in various insulating forms such as the fully reduced leucoemeraldine base (LEB), half-oxidized, emeraldine base (PANiEB) and fully-oxidized, pemigraniline base (PNB). Of these three forms, PANiEB is the most stable and widely investigated polymer in this family. PANiEB differs substantially from LEB and PNB in the sense that its conductivity can be tuned via doping from $10^{-10}$ up to 100 Siemens per cm and more whereas the LEB and PNB forms cannot be made conducting. Thus a doped PANiEB may be formed as a suitable RF energy dissipation material. See for example, Pure and Applied Chemistry Vol. 74, pages 857-867 (2002).

An Integrated Approach to MRI Compatibility:

An integrated approach to MRI compatibility involves a lead assembly simultaneously satisfying the following conditions: a. there are no susceptibility effects from materials used for the lead construction to avoid image artifacts; b. the materials used are non-magnetizable to avoid image artifacts; c. the lead design minimizes build up of induced common mode currents while the lead is being exposed to the MRI RF field; d. the lead design avoids formation low frequency (0.001 kHz-10 kHz) conductive loops so that the lead structure is unaffected by the gradient field; e. the lead is flexible enough to be usable for long term bio implant use, for example, in electrical stimulating devices such as cardiac pacemakers, defibrillators, and nerve stimulators; and f. the lead is biocompatible such that it does not promote or cause any adverse reaction to the user. Thus, a key aspect of the invention is achieving simultaneous electrical, mechanical and biological compatibility.

Achieving Electrical Compatibility:

The electrical compatibility is established by minimizing build up of the induction of the common mode current as described below: First approach involves a lead, for example, a transmission line type quad filar lead, forming as a transmission line with a self resonant frequency, equal to the MR frequency while in the body as described earlier. The lead is constructed to provide parallel resonance, and thus present very high impedance at the resonant frequency, while appearing inductive below resonance frequency and capacitive above resonance frequency. This method is useful for the higher MR field strengths such as 3.0 T, where the image quality aspects of the lead are a bigger challenge as compared to 1.5 T or lower. A second approach involves placing RF blocking networks in the lead at least quarter wavelength locations as described earlier. Note that for 3.0 T the wavelength is half that of the 1.5 T field strength. Thus, to address the issue for these two field strengths, the networks would be placed at the quarter wavelength of the highest frequency (approximately 128 MHz) encountered. For the lower 1.5 T frequency there would thus be redundant networks as they would appear at every ⅛ wavelength. However, this redundancy does not adversely affect the blocking function. A third approach involves using a combination of the first and the second approaches. A fourth approach involves reducing the ability of the lead to be an antenna, i.e. a receptacle for RF energy. If the lead could be presented to the surrounding field as a low quality antenna, the amount of energy absorbed would be reduced. This quality reduction can be accomplished by adding damping to the lead, or a way to dissipate the absorbed energy in such a way that no focal spots in the E field will exist. Since focal spots in the E-field can be created by concentration of E-field, such as at tips or ends of wires or components, any sharp edge or point is avoided. For non-sharp objects such as lead conductors, further energy damping can be provided by coating the lead conductor with a medium grade conductor, so as to provide sufficient resistivity to dissipate energy. This approach is further described with the following three configurations.

Figure 13:
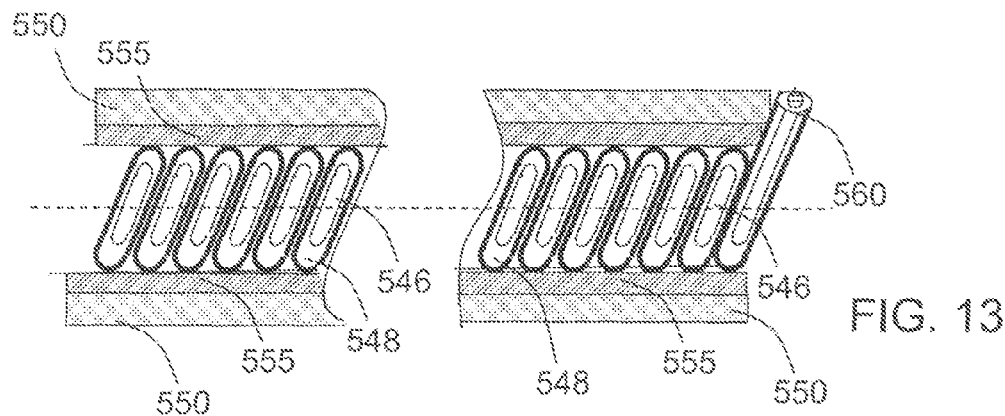
FIG. 13 is a schematic longitudinal view through a lead assembly with a single layer, multiple coil configuration.

Prevention of Lead Becoming an Antenna:

Single layer multi-wire lead configuration: Referring to FIG. 13, a single layer, multi-wire lead comprises of single coiled conductors such as 546 covered by insulation 548 forming the central structure. The insulated, coiled conducting wires are coated by a layer 555 of medium conductive material mentioned before. The entire structure is covered by a biologically compatible insulating layer 550. The distal part of the lead less than one eighth of the wavelength need not be coated with a medium conductive coating 555. The conductive wires in the lead usually terminate in an electrode (not shown) that is in contact with the tissue to be stimulated. One such terminus 560 is shown in the FIG. 13. Note that if there are multiple coils, each one of them will have a terminus similar to 560. Further note that in this configuration, all the coiled conductors are in one layer.

Figure 14:
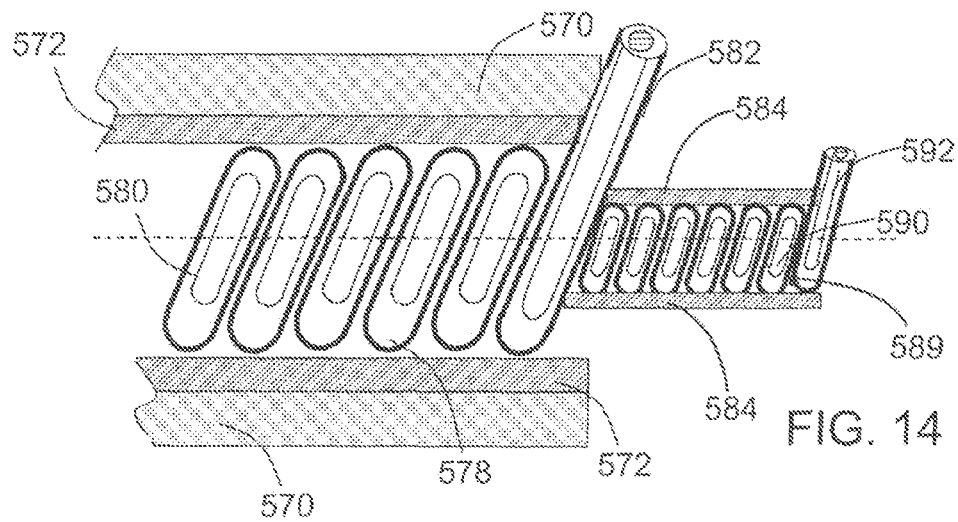
FIG. 14 is a schematic longitudinal view through a lead assembly with a multi-layer, multiple coil configuration.

Multi-layer, multi-wire lead configuration: Referring to FIG. 14, it can be seen that this configuration is similar to the previously described configuration except for the presence of multiple layers of conductors. An example of this type could be a bi-filar configuration in which there are two layers of coils with each layer having two coiled conductive wires. Different layers are separated by spacers 584. In the above mentioned bi-filar configuration, two termini from the outer layer and two termini from the inner layer are available for connecting to the electrode elements (not shown). Referring to FIG. 14, a two layer, multi-wire lead comprises of multiple coiled outer conductors such as 580 covered by insulation 578 forming the central structure and inner conductors such as 590 covered by insulation 589 forming the central structure. The insulated, coiled outer conducting wires are coated by a layer 572 of medium conductive material mentioned before which layer is biologically compatible and electrically insulating. The distal part of the lead less than one-eighth of the wavelength need not be coated with a medium conductive layer 572. The conductive wires in the lead usually terminate in an electrode (not shown) that is in contact with the tissue to be stimulated. One such terminus 582 is shown in the FIG. 14. Note that if there are multiple coils, each one of them will have a terminus similar to terminus 582.

Figure 15A:
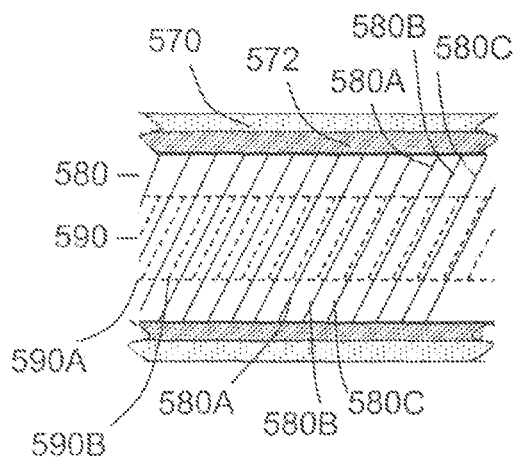
FIGS. 15A and 15B schematically show longitudinal views of two alternative ways of winding conductors in a lead assembly with a multi-layer, multiple coil configuration.
Figure 15B:
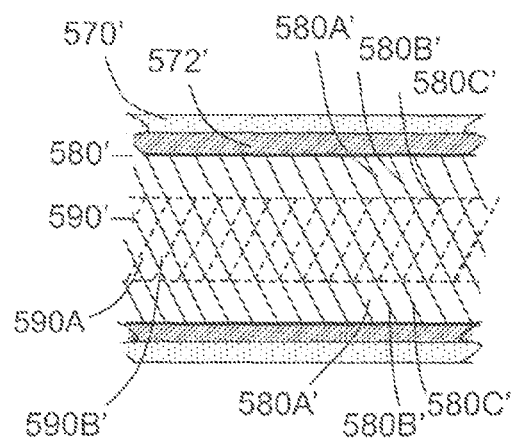

FIGS. 15A and 15B further illustrate alternative arrangements possible with variations in winding directions in a bi layer, bi filar example. In this example, it should be noted that both inner and outer layers have multiple insulated conductors wound on each layer. The number of insulated conductors for these two layers may be the same or they may be different. In one embodiment, FIG. 15A shows three insulated conductors 580A, 580B and 580C are wound on the outer layer and two insulated conductors 590A and 590B are wound on the inner layer. An optional spacer layer (not shown) may be present between inner and outer layers. The winding directions of insulated outer conductors 580 may be in the same direction of the insulated inner conductors 590 as shown in FIG. 15A or they may be in different direction as shown in FIG. 15B. In some embodiments, the medium conductivity coating 572 and the external biocompatible layer 570 may be separate layers as shown in FIG. 15A. In an alternative embodiment, these layers may be combined into one layer. This would be the case when the medium conductive material also happens to be biologically compatible. In any case, the external layer is in contact with a body tissue or body fluids.

Figure 16A:
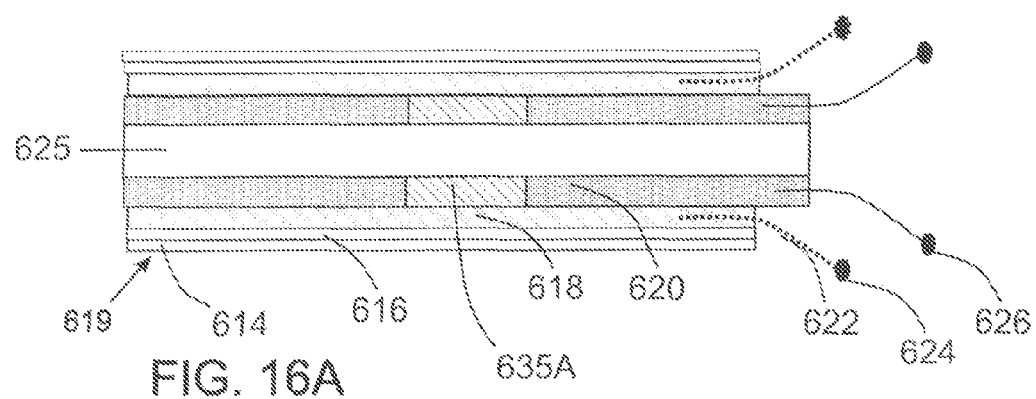
FIGS. 16A and B schematically illustrate longitudinal views of the lead assembly with a multi-layer, multiple coil configuration in compressed and extended states, respectively.
Figure 16B:
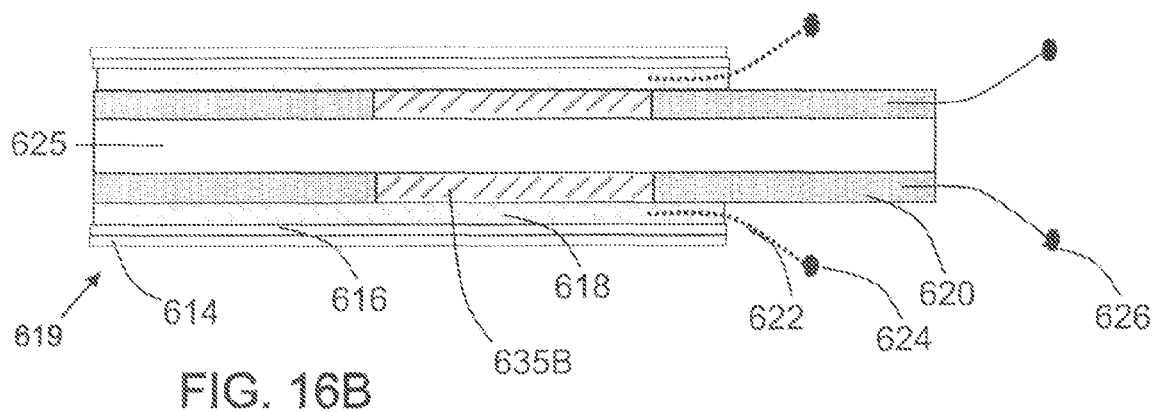

Multi-layer, multi-wire lead configuration with adjustable electrode distance: Now referring to FIGS. 16A and 16B, we illustrate a special type of lead 619 which is similar to the previous multi-layer, multi-wire lead configuration of FIGS. 14 and 15 but with a key difference. The inside layer is designed to be adjustable so that the distances between electrodes 624 and 626 connected to the coiled wire termini can be adjusted during the implantation. Thus the extendable lead 619 allows for deployment of electrodes at locations with variable distance as shown by the extension of original space 635A in FIG. 16A to extended space 635B in FIG. 16B. The lead 619 is composed of an outer layer 618 and inner 620 layer, each having one or more coiled insulated conductors. The inner layer contains a section which can be extended or contracted by means of an inner guide wire or sheath (not shown) that can be brought in through the central space 625. Since locations of stimulation or sensing in an organ, for example, heart, is not accurately predictable and varies amongst individuals, usually multiple leads are inserted to reach two locations for sensing and or stimulation. This configuration allows a single lead to fulfill this need, obviating the need for multiple leads and simplifying the procedure. When the inner lead is extended, it does change the overall length of the lead structure, but without changing the length at the other, non-extendable end. In one embodiment shown in FIGS. 16A and 16B, when the extension range is less than 7.6 cm, one may not use the extra layers of medium conducting material and the metal patches at quarter wavelength intervals on the extended part of the lead. In this embodiment, a medium conducting layer and a biocompatible insulating layer are also added over the conductors on the extended part.

Referring to FIG. 16, an adjustable two layer, multi-wire lead 619 comprises of multiple coiled outer layer of conductors 618 covered by insulation and inner layer of conductors 620 covered by insulation forming the central structure. The insulated, coiled outer conducting wires are coated by a layer 616 of medium conductive material defined previously, which layer is biologically compatible and electrically insulating. The distal part of the lead 619 less than one-eighth of the wavelength need not be coated with a medium conductive layer 616. The conductive wires in the lead 619 usually terminate at a terminus 622 and an electrode 624 or 626 that are in contact with the tissue to be stimulated. The terminus 622 is a bare, non-insulated portion of a conductor in the outer layer of conductors 618 which is adapted to be exposed to body tissue or body fluids upon implantation in an animal. The length of the terminus 622 is determined by a wavelength which is a function of the velocity (v) of the electromagnetic wave in the animal tissue divided by the frequency of the electromagnetic wave. The velocity is the inverse of the square root of the product of permittivity and permeability of the tissue. Therefore the terminus length (L) is defined by the expression $L<(\frac{1}{4})(v/f)$, where (f) is the Larmor frequency of a magnetic resonance imaging scanner. In an exemplary embodiment where there are two coils in the inner conductive wires and two coils in the outer conductive wires, each of those conductive wires has a separate terminus and electrode.

In the configurations described above, the coil turns per unit distance, coil structure diameters, distance between inner and outer insulated conductors, conductivity of a layer of medium conducting material, dielectric medium between the conductors as characterized by relative permittivity of the dielectric, and total length of the lead are adjustable parameters that can be chosen based on the field strength of the MRI scanner. Additionally, the transmission line characteristic impedance (CI) is also an important design parameter. This is the virtual impedance of any wire pair. For example, television coaxial cables have a typical characteristic impedance of 50, 60 or 75 Ohm; for telephone lines, the CI is 600 Ohm; and for ribbon cable with 1.3 mm pitch, CI is 110 Ohm. In the present case, there may be two transmission lines, inner and outer, each with their own CI in the range of 10 to 1000 Ohm.

The above parameters have the following preferred ranges of values: turns per unit length may be same or different for the inner and outer layer of conductors with a range of 4 turns per centimeter to 40 turns per centimeter; conducting wire diameter: 0.05 mm to 0.0025 mm; inner coil diameter: 0.635 mm to 1.524 mm; outer coil diameter: 0.76 mm to 2.54 mm; dielectric thickness: 0.0025 mm to 0.5 mm; relative permittivity of dielectric: 1 to 15; conductivity of the medium conductive layer: 0.001 S/m and 200 S/m; and the total length of the lead is chosen based on the physiological requirement and MRI field strength.

MRI Compatible Defibrillation Lead:

For an MR compatible defibrillation (ICD) lead, the lead coil section that forms one of the contacts, is not modified for MRI compatibility. It does not contain any materials that have a magnetic moment, such as soft iron, nickel or cobalt, as their presence would cause image artifacts. If the unmodified section is less than any quarter wavelength (in body fluid) of the MRI scanner, there will not be any image quality (IQ) issues. In general the IQ issues increase with field strength, with most issues anticipated at the common 1.5 T and 3.0 T field strengths. In these cases a 5 to 7 cm segment may be left partially unmodified, without causing significant adverse IQ affects. It should be noted that a pacing lead can also be left unmodified over the last 5 cm to 7 cm segment without causing adverse MR IQ effects in 1.5 T or 3.0 T imagers.

Figure 17A:
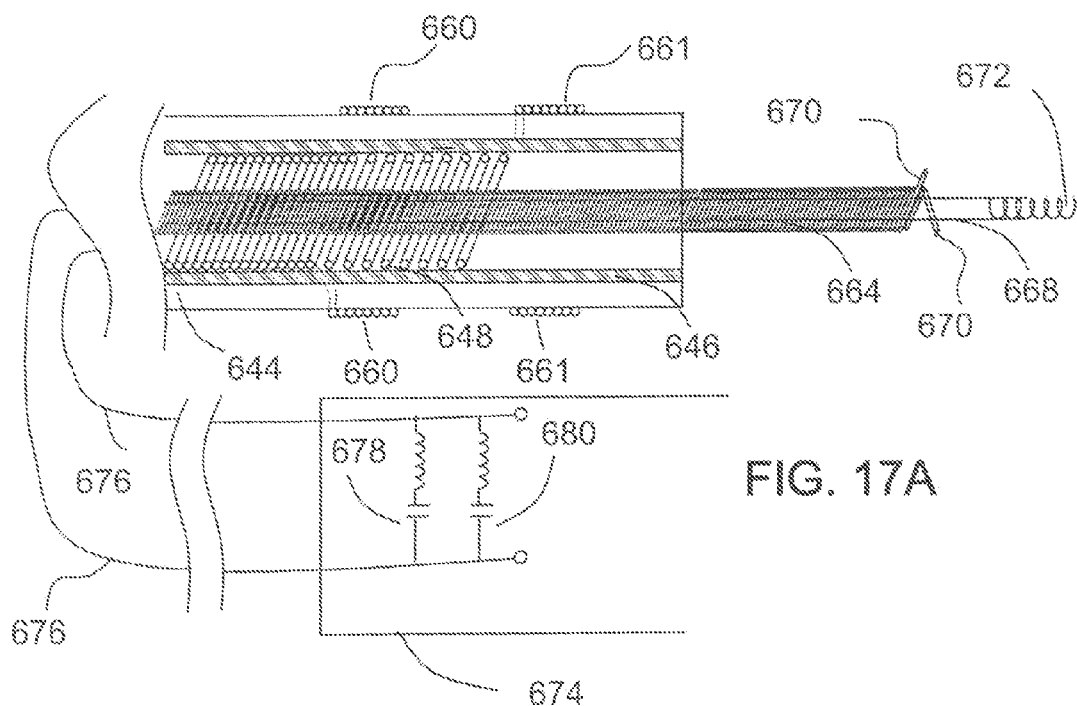
FIG. 17A is a schematic of the MRI compatible defibrillation lead with series resonant circuits across the lead.

Referring to FIG. 17A, a defibrillation lead comprises of multiple coiled conductors such as 648 covered by insulation forming the central structure. The insulated, coiled conducting wires 648 are coated by a layer 646 of medium conductive material mentioned before. The entire structure is covered by a biologically compatible insulating layer 644. In an exemplary case of two electrode defibrillator, the insulated conductor comes out of the lead body without insulation and is wound on the lead body without touching each winding of the coil as electrodes 660 and 661.

The proximal end of the insulated conductors are connected to a series resonant circuits 678 and 680 which are tuned to short out the defibrillator circuit at the resonant frequencies of 1.5 T scanner (64 MHz) and 3.0 T scanner (128 MHz) respectively. Similar series resonant circuits may be provided for other scanners as well. The resonant circuits are housed in the ICD container 674.

Figure 17B:
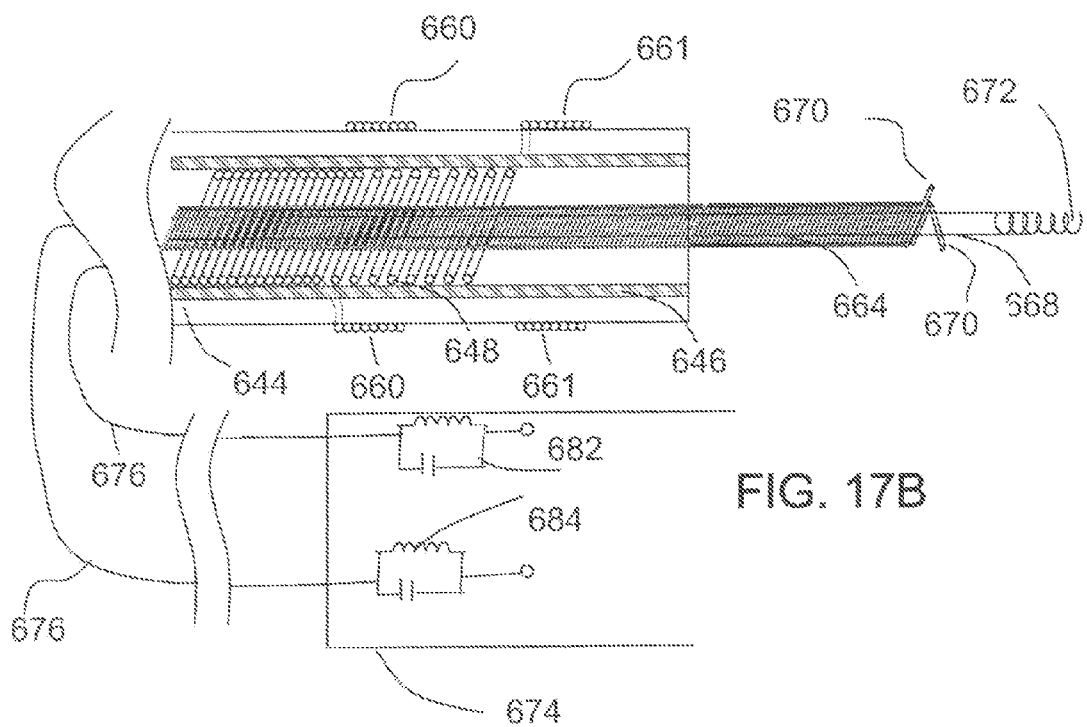
FIG. 17B is a schematic of the MRI compatible defibrillation lead with parallel resonant circuits along the lead.

Alternatively, as shown in FIG. 17B, the proximal end of the insulated conductors are connected in series to parallel resonant circuits 682 and 684 which are used for blocking any MRI induced current. The resonant circuits are housed in the ICD container 674.

Additionally, the inner coiled insulated conductor 664 is for cardiac pacing. The end termini 670 are connected to the pacing electrodes (not shown). If the inner insulated conductor for pacing is more than one-eighth of a wavelength of the MRI scanner in contact with the body fluid or tissue for pacing, then the medium conducting coating covers the surface of the inner conductor 664 followed by an outer insulating layer. The inside tube 668 is present through out the lead and is terminated with an anchoring component 672 which helps in the anchoring of the lead. The anchoring component is made up of an MRI compatible material described earlier.

Achieving Mechanical and Biological Compatibility:

The mechanical and biological compatibility is obtained using the steps described below: First, the flexibility of the lead is required to allow for the lead to follow the body and intra-organic movements, without impediment. Second, the fatigue resistance is essential for many applications, for example, in a cardiac apex application, the lead end would flex with each heart beat. Third, considerations are given to satisfy both flexibility and fatigue resistance simultaneously in addition to providing biocompatibility. Polyurethane materials are used for the lead body to meet all the three criteria. In addition, the conductor material is chosen from the well known alloys, for example, MP35, stainless steel, which are specifically designed to have a very high fatigue resistance and tensile strength against breakage.

Referring to FIGS. 4 and 7, the housing 42 of the implantable medical device 40 also has been uniquely constructed to be compatible with an MRI scanner. FIG. 7 shows a cross section through one exterior walls 66 of that housing 42. The wall is electrically conductive to shield the internal electronic circuitry from radio frequency interference during normal operation. Specifically, the housing walls are conductive at RF frequencies, but have high impedance at the frequency associated with the leading and trailing edges of the MRI gradient pulses, thus preventing gradient eddy currents in the walls. The exemplary wall 66 is formed by outer conducting layers 52 and 54 of aluminum, copper, or other electrically conductive, non-ferromagnetic material applied to the major surfaces of a substrate 56 of dielectric material, thereby forming a laminated wall with the substrate sandwiched between two conductive layers. The first layer 52 is on the exterior surface 51 of the substrate 56, and the conducting second layer 54 is on the interior surface 53 of the substrate.

A plurality of slots 58 and 60 are made through the first and second layers 52 and 54, respectively, to expose dielectric substrate 56, thus creating a plurality of conductive segments 62 and 64 which form stripes on the opposing surfaces of the substrate 56. The first slots 58 in the first layer 52 are offset in the plane of the wall from the second slots 60 in the second layer 54 so that there is not a direct electrical path through both layers 52 and 54. RF continuity is ensured via the capacitance coupling created through the dielectric substrate 56 between opposing conductive segments 62 and 64. The spacing between the slots on each dielectric surface is a function of the slew rate or rise time of the MRI gradient signal. Shorter rise times of the gradient pulses require smaller metallic surfaces to keep gradient eddy currents to an acceptable predefined level which will not adversely affect the animal. For example, a typical MRI gradient signal pulse requires each conductive segment 62 and 64 to be ten square centimeters or less.

With respect to FIG. 4, note that the slots 58 in one wall 66 of the housing 42 are not aligned with nor parallel to the slots 58 in an adjacent abutting wall 67 or 68. The same is true for the hidden walls in the drawings. A slot 58 also extends along each corner of the housing where two walls meet, so that the conductive segments 62 in the walls are not electrically connected. The same misalignment exists on the interior surfaces of the walls.

FIG. 8 illustrates an alternative arrangement of the slots in the outer surface 51 of the housing 42. A first group of slots 80 extend transversely, preferably orthogonally, to a second group of slots 82, thereby forming a two dimensional array of conductive segments 84 in the electrically conductive first layer 86. A similar arrangement of transverse groups of slots form another two dimensional array of conductive segments on the second layer that forms the interior surface of the wall. The exterior and interior arrays are offset in both directions to overlap thereby capacitively coupling the first and second layers.

Implantable Enclosure with an Antenna:

An implantable enclosure with an integrated antenna provides another challenge for MRI compatibility. The antenna may be used for powering the implanted device or for communication with an external device unidirectionally or bidirectionally.

In general implanted devices are contained in a metallic or conductive container. Usually this container is also serving as an electromagnetic interference (EMI) shield, protecting the contained electronics from external electrical or magnetic noise. This noise can potentially interfere with the function of the device as it may cause corruption of the physiological data that is being gathered. The signal levels of physiological data tends to be very small, e.g., tens or hundreds of microvolts for neural signals, one to tens of millivolts for muscle signals. Ambient electrical noise (i.e. EMI) field strengths in home, store, office or industrial environments can be anywhere from one volt per meter to hundreds of volts per meter and set up induced noise levels in the body that can easily be many times larger than the signal of interest.

As a consequence the standard method is to shield the sensitive electronics with a conductive enclosure, thus presenting a Faraday cage or shield. The disadvantage of this method is that in order for a power or communication antenna to work, the antenna has to be positioned outside of that enclosure, as an internal antenna would not be able to receive or transmit effectively through the Faraday shield.

The solution to this problem involves making use of an alternative EMI prevention method involving a magnetic field antenna and a non-conductive enclosure. These changes permit the power and/or communication antenna to be placed inside the enclosure or be integrated in the enclosure itself. These novel modifications are described in further detail below.

Figure 18:
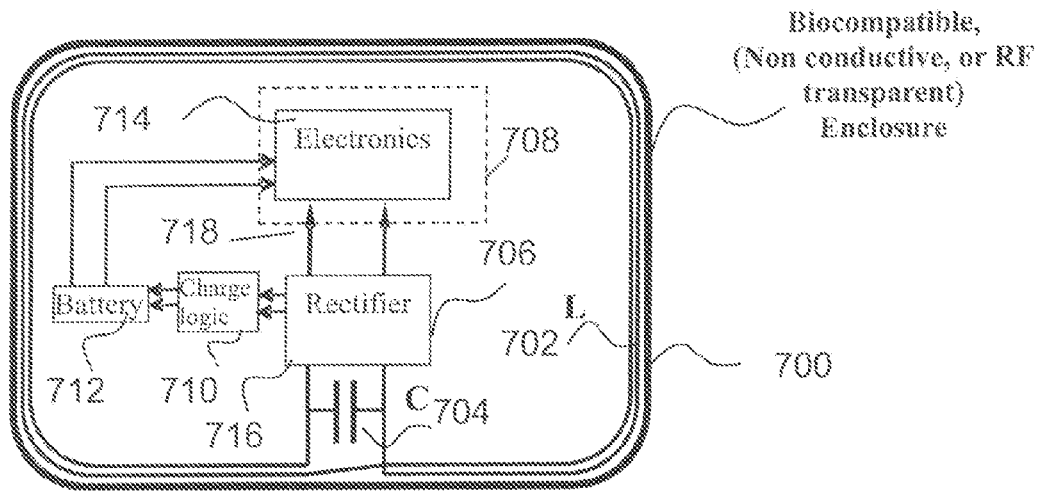
FIG. 18 is the schematic of an MRI compatible power antenna and associated shielded electronic circuitry inside an RF transparent enclosure.

Power Antenna:

As shown in FIG. 18, a magnetic field power antenna module comprises of an inductor element 702 which is looped around inside an enclosure casing 700. Alternatively, a coil pattern may be formed inside the enclosure to serve a similar purpose. The inductor L forms an inductive pickup loop and the two ends of this loop are connected to a capacitor 704. L and C form a resonant tank circuit, allowing for maximum energy transfer at the frequency $F=1/\sqrt{2\pi LC}$. This power antenna is well suited for highly efficient, resonant transfer of energy. The energy is converted to DC by the rectifier 706 and is used by the electronic circuit 714 for providing therapy and or data acquisition. The enclosure casing 700 is biocompatible, non-conductive and radio frequency transparent. The electronic circuit 714 is enclosed by an electromagnetic shield 708 which is similar to the housing 42 described in detail with reference to FIG. 7. Alternatively, it may be connected to a ground plane. For the EMI shielding of the case or the electronics, a mesh may be used. In the MR scanner phosphor bronze and stainless steel meshes with a wire density of 128 lines per centimeter may be used in an exemplary case. These meshes have good conductivity at radio frequencies, but have high impedance at the MRI gradient frequency.

The power induced by external power supply (not shown) to the antenna mentioned above may be bypassed by a command to the charge logic 710. In that case, the shielded internal electronics circuit is powered by an internal battery 712, which may be a traditional battery or a rechargeable battery that is recharged via energy efficient, resonant inductive coupling mentioned before.

Figure 19:
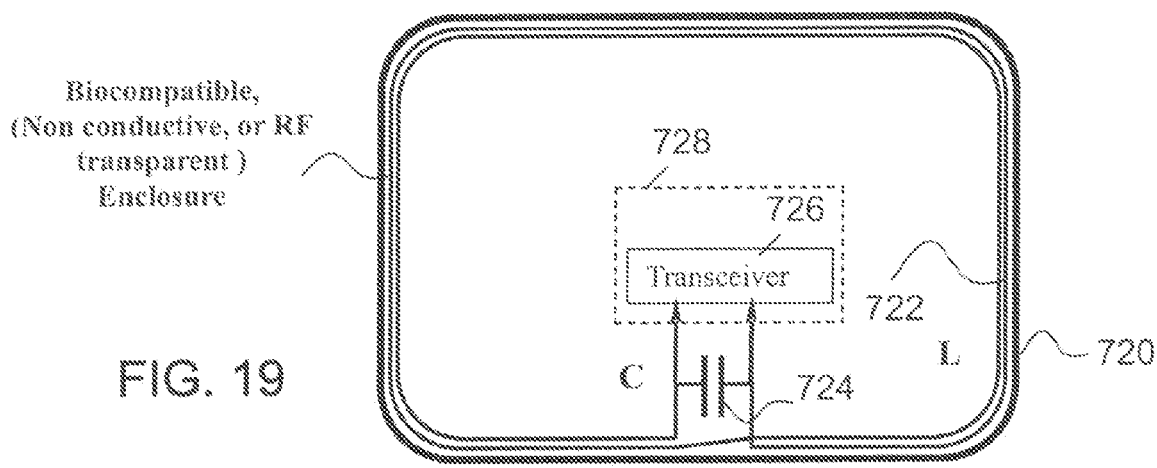
FIG. 19 is the schematic of an MRI compatible communication antenna and associated shielded transceiver circuitry inside an RF transparent enclosure.

Communication Antenna:

As shown in FIG. 19, a communication antenna module is formed inside an enclosure casing 720, with loops of inductive wire L 722 forming a pickup loop. Alternatively, a coil pattern may be formed inside the enclosure to serve a similar purpose. The ends of the loop are connected to the capacitor C 724. Elements L and C form a resonant tank circuit, allowing for maximum energy transfer at the frequency $F=1/\sqrt{2\pi LC}$. The tank circuit may be a part of the data communication and reception that is performed by a transceiver 726. The enclosure casing 720 is biocompatible, non-conductive and radio frequency transparent. The transceiver 726 may be enclosed by an electromagnetic shield 728 which is similar to the housing 42 described in detail with reference to FIG. 7. Alternatively, it may be connected to a ground plane. For the EMI shielding of the case or the electronics, a mesh may be used. In the MR scanner phosphor bronze and stainless steel meshes with a wire density of 128 lines per centimeter may be used in an exemplary case. These meshes have good conductivity at radio frequencies, but have high impedance at the MRI gradient frequency.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

We claim:

1. An implantable electrical lead that is biocompatible upon implantation in an animal and compatible with a magnetic resonance imaging scanner for the purpose of diagnostic quality imaging, wherein the magnetic resonance imaging scanner is responsive to signals at a Larmor frequency, said implantable electrical lead comprising:
   a first plurality of coiled insulated conducting wires wound in a first direction forming an outer layer of conductors having a first total length with a first number of turns per unit of length;
   a second plurality of coiled insulated conducting wires wound in a second direction forming an inner layer of conductors within the outer layer and having a second total length with a second number of turns per unit of length;
   a layer of dielectric material separating the inner layer and the outer layer by a distance, wherein the distance and properties of the dielectric material create a high impedance at the Larmor frequency of the magnetic resonance imaging scanner;
   an electrically conductive layer around the outer layer of conductors; and
   a mechanically flexible, biocompatible layer forming an external layer of the implantable electrical lead and adapted to contact with body tissue or body fluids of an animal.

2. The implantable electrical lead as recited in claim 1 wherein the electrically conductive layer is formed on the outer layer of conductors.

3. The implantable electrical lead as recited in claim 1 further comprising an electrode connected to the first plurality of coiled insulated conducting wires for stimulating the animal.

4. The implantable electrical lead as recited in claim 3 further comprising an electrode connected to the first plurality of coiled insulated conducting wires for cardiac pacing the animal.

5. The implantable electrical lead as recited in claim 3 further comprising an electrode connected to the first plurality of coiled insulated conducting wires for performing a cardiac defibrillation on the animal.

6. The implantable electrical lead as recited in claim 1 wherein the first direction in which the first plurality of coiled insulated conducting wires are wound is different than the second direction in which the second plurality of coiled insulated conducting wires are wound.

7. The implantable electrical lead as recited in claim 1 wherein the first direction in which the first plurality of coiled insulated conducting wires are wound is the same as the second direction in which the second plurality of coiled insulated conducting wires are wound.

8. The implantable electrical lead as recited in claim 1 wherein the electrically conductive layer has a conductivity between 1.00 and $10^4$ Siemens per meter.

9. The implantable electrical lead as recited in claim 1 wherein the Larmor frequency is one of 64 MHz and 128 MHz.

10. The implantable electrical lead as recited in claim 1 wherein the high impedance created by properties of the dielectric material and the distance separating the inner layer and the outer layer prevent currents from forming in the lead due to electromagnetic fields of the magnetic resonance imaging scanner.

11. The implantable stimulation lead as recited in claim 1 wherein the electrically conductive layer comprises a material that has electrically conductive, non-magnetizable particles in physical contact with each other.

12. The implantable stimulation lead as recited in claim 1 wherein the first plurality of coiled insulated conducting wires and the second plurality of coiled insulated conducting wires extend from one end of the implantable electrical lead to another end.

13. An implantable stimulation lead compatible with a magnetic resonance imaging (MRI) scanner for the purpose of diagnostic quality imaging, wherein the magnetic resonance imaging scanner produces a signal at a Larmor frequency, said implantable stimulation lead comprising:
   a first plurality of insulated conducting wires wound in a first direction around a central axis to form an inner layer of electrical conductors of the lead;
   a second plurality of insulated conducting wires wound in a second direction around the central axis and over the first plurality of insulated conducting wires, thereby forming an outer layer of conductors of the lead, wherein at least two wires of the second plurality of insulated conducting wires each have a section of a non-insulated conductor projecting outwardly from the lead to form electrodes;
   a layer of dielectric material separating the inner layer and the outer layer by a distance, wherein the distance and properties of the dielectric material create a high impedance at the Larmor frequency of the magnetic resonance imaging scanner; and
   a conductive coating on one of the inner layer of conductors and the outer layer of conductors, wherein the coating comprises a material having electrically conductive, non-magnetizable particles in physical contact with each other.

14. The implantable stimulation lead as recited in claim 13 wherein each of the first and second plurality of insulated conducting wires having a proximal end; and further comprising two parallel resonant circuits each connected to a different proximal end for blocking currents induced in the implantable stimulation lead by the magnetic resonance imaging scanner.

15. The implantable stimulation lead as recited in claim 13 further comprising a separate component terminating each section of the non-insulated conductor and formed of an MRI compatible material for anchoring the section into tissue of an animal.

16. The implantable stimulation lead as recited in claim 13 further comprising:
   an electrode connected to the outer layer of conductors for performing cardiac defibrillation; and
   another electrode connected to the inner layer of conductors for performing cardiac pacing.

17. The implantable stimulation lead as recited in claim 13 wherein the coating of the conducting layer has a conductivity between 1.00 and $10^4$ Siemens per meter.

18. The implantable stimulation lead as recited in claim 13 wherein the Larmor frequency is one of 64 MHz and 128 MHz.

19. The implantable stimulation lead as recited in claim 13 wherein the conducting coating is on the outer layer of conductors.

20. The implantable stimulation lead as recited in claim 13 wherein the conducting coating has a lumen through which the inner layer of conductors and the outer layer of conductors extend.

21. The implantable stimulation lead as recited in claim 13 wherein the first plurality of coiled insulated conducting wires and the second plurality of coiled insulated conducting wires extend from one end of the implantable electrical lead to another end.

22. An implantable biocompatible electrical lead that also is compatible with a magnetic resonance imaging scanner for the purpose of diagnostic quality imaging, said implantable biocompatible electrical lead comprising:
   a first plurality of coiled insulated electrical conductors wound in a first direction forming an inner layer of conductors;
   a second plurality of coiled insulated electrical conductors wound in a second direction forming an outer layer of conductors; and
   a dielectric material between the inner and outer layers;
   wherein a number of turns of the inner and outer layers of electrical conductors per unit of length of the implantable biocompatible electrical lead, the distance between the inner and outer layers, properties of the dielectric material, and a total length of the implantable biocompatible electrical lead create a high impedance at a frequency of an electromagnetic field produced by the magnetic resonance imaging scanner.

23. The implantable biocompatible electrical lead as recited in claim 22 further comprising:
   an electrically conductive layer having a lumen through which the inner layer of conductors and the outer layer of conductors extend and having an electrical conductivity between 1.00 and $10^4$ Siemens per meter and comprising a material that has electrically conductive, non-magnetizable particles in physical contact with each other; and
   a mechanically flexible, biocompatible layer forming an external layer of the implantable electrical lead that is adapted to contact tissue or body fluids of an animal.

24. The implantable biocompatible electrical lead as recited in claim 23 wherein the conductive layer is formed on the outer layer of conductors.

25. The implantable biocompatible electrical lead as recited in claim 22 further comprising an electrode for stimulating tissue of an animal.

26. The implantable biocompatible electrical lead as recited in claim 22 further comprising an electrode for stimulating an organ of an animal, wherein the organ is one of heart, brain, ear, stomach, prostate, urinary bladder, pancreas, liver, and spine.

27. The implantable biocompatible electrical lead as recited in claim 22 further comprising an electrode for performing a cardiac defibrillation on an animal.

28. The implantable biocompatible electrical lead as recited in claim 22 further comprising an electrode for sensing electrical signals in an animal.

29. The implantable biocompatible electrical lead as recited in claim 28 further comprising an electrode for stimulating tissue of an animal.

30. The implantable biocompatible electrical lead as recited in claim 22 wherein the first direction and the second direction are the same.

31. The implantable biocompatible electrical lead as recited in claim 22 wherein the first direction and the second direction are different.

32. The implantable biocompatible electrical lead as recited in claim 22 wherein each of the first and second plurality of coiled insulated electrical conductors has a portion without insulation that is adapted to be exposed to body tissue or body fluids upon implantation in an animal, wherein the portion has a length that is less than a quarter wavelength in the body tissue at the frequency of an electromagnetic field produced by the magnetic resonance imaging scanner.

33. The implantable stimulation lead as recited in claim 22 wherein the frequency of the electromagnetic field is one of 64 MHz and 128 MHz.

34. The implantable stimulation lead as recited in claim 22 wherein the first plurality of coiled insulated conducting wires and the second plurality of coiled insulated conducting wires extend from one end of the implantable electrical lead to another end.

35. An implantable electrical lead that is biocompatible upon implantation in an animal and compatible with a magnetic resonance imaging scanner, said electrical lead comprising:
   a plurality of insulated conducting wires wound in a coil to form a layer of conductors extending from one end of the implantable electrical lead to another end and having a number of turns per unit of length selected to create a high impedance at the frequency of an electromagnetic field produced by the magnetic resonance imaging scanner;
   an electrically conductive layer comprising a non-magnetizable material, which is remote from contact with body tissue or body fluids of the animal; and
   a flexible, biocompatible layer forming an external layer of the implantable electrical lead and adapted to contact with body tissue or body fluids of an animal.

36. The implantable stimulation lead as recited in claim 35 wherein the frequency of the electromagnetic field is one of 64 MHz and 128 MHz.

37. An stimulation lead that is biocompatible upon implantation in an animal while in a magnetic resonance imaging scanner for the purpose of diagnostic quality imaging, said stimulation lead comprising:
   a plurality of coiled insulated conducting wires wound to form a layer of conductors extending from one end of the implantable electrical lead to another end and having a number of turns per unit of length selected to create a high impedance at the frequency of an electromagnetic field produced by the magnetic resonance imaging scanner;
   an electrically conductive layer comprising a non-magnetizable material with a conductivity between 1.00 and $10^4$ Siemens per meter, and which is remote from contact with body tissue or body fluids of the animal; and
   a mechanically flexible, non-longitudinally compressible, biocompatible layer forming an external layer of the stimulation lead and adapted to contact with body tissue or body fluids of an animal.

38. The implantable stimulation lead as recited in claim 37 wherein the frequency of the electromagnetic field is one of 64 MHz and 128 MHz.

* * * * *